US012752073B2

United States Patent
(12) United States Patent
Starr

(10) Patent No.: US 12,752,073 B2
(45) Date of Patent: Oct. 6, 2026

(54) THERAPEUTIC WEARABLE ARTICLES

(71) Applicant: Kera Wear, Inc., Scottsdale, AZ (US)

(72) Inventor: Kerry Starr, Scottsdale, AZ (US)

(73) Assignee: Kera Wear, INC., Scottsdale, AZ (US)

( * ) Notice: Subject to any disclaimer, the term of this patent is extended or adjusted under 35 U.S.C. 154(b) by 794 days.

(21) Appl. No.: 18/026,796

(22) PCT Filed: Sep. 17, 2021

(86) PCT No.: PCT/US2021/050839
§ 371 (c)(1),
(2) Date: Mar. 16, 2023

(87) PCT Pub. No.: WO2022/061090
PCT Pub. Date: Mar. 24, 2022

(65) Prior Publication Data

US 2023/0321390 A1 Oct. 12, 2023

Related U.S. Application Data

(60) Provisional application No. 63/081,115, filed on Sep. 21, 2020.

(51) Int. Cl.
*A61M 21/00* (2006.01)
*A41D 27/00* (2006.01)

(52) U.S. Cl.
CPC ............. *A61M 21/00* (2013.01); *A41D 27/00* (2013.01); *A41D 2400/32* (2013.01); (Continued)

(58) Field of Classification Search
CPC .......... A61M 21/00; A61M 2021/0016; A61M 2209/088; A61M 35/10; A41D 27/00; A41D 2400/32; A41D 2600/00; A41B 2400/32; A61F 13/00063; A61F 13/061; A61F 13/064; A61F 13/068; A61F 13/10;
(Continued)

(56) References Cited

U.S. PATENT DOCUMENTS 4,277,024 A * 7/1981 Spector .................... A61L 9/12
206/466
4,283,011 A * 8/1981 Spector .................... A61L 9/12
239/57
(Continued)

OTHER PUBLICATIONS

European Search Report for European Application No. 21870279.3, mailed Sep. 10, 2024, 7 pages.
(Continued)

*Primary Examiner* — Sunita Reddy
(74) *Attorney, Agent, or Firm* — Ganz Law, PC

(57) ABSTRACT

A wearable article, comprising a treatment delivery system, the system having a pliable assembly of layers, including an absorbent layer or other receptacle layer having a surface for absorbing or containing a treatment agent and intended to orient against a wearer's skin (dermal embodiment) or outside of the article oriented towards the wearer's olfactory system (aromatherapy embodiment); a base layer for the wearable article; a barrier or other backing layer for selectively blocking the passage of the treatment agent, while preferably allowing skin moisture to pass through the backing layer disposed between the receptacle layer and the backing layer.

25 Claims, 5 Drawing Sheets

(52) U.S. Cl.
CPC . *A41D 2600/00* (2013.01); *A61M 2021/0016* (2013.01); *A61M 2209/088* (2013.01)

(58) Field of Classification Search
CPC ...... A61F 13/104; A61F 13/107; A61F 13/12; A61F 13/14
USPC ...................................................... 600/26–28
See application file for complete search history.

(56) References Cited

U.S. PATENT DOCUMENTS

| | | | |
|---|---|---|---|
| 4,937,020 A | 6/1990 | Wagner et al. | |
| 5,114,631 A | 5/1992 | Nyssen et al. | |
| 5,395,047 A * | 3/1995 | Pendergrass, Jr. | A61L 9/12 428/905 |
| 5,614,202 A | 3/1997 | Defina | |
| 5,720,046 A * | 2/1998 | Lopez | A43B 1/0054 2/160 |
| 5,950,239 A * | 9/1999 | Lopez | A42B 1/24 2/113 |
| 6,824,372 B2 | 11/2004 | Berrigan et al. | |
| 7,655,175 B2 | 2/2010 | Michael et al. | |
| 7,857,608 B2 | 12/2010 | Febbricante et al. | |
| 8,231,378 B2 | 7/2012 | Lozano et al. | |
| 8,425,810 B2 | 4/2013 | Ishikawa et al. | |
| 9,956,387 B2 | 5/2018 | Brown | |
| 2002/0142027 A1 | 10/2002 | Gueret | |
| 2003/0014096 A1 | 1/2003 | Burkhart | |
| 2004/0247528 A1* | 12/2004 | Schoneberg | A61N 2/06 424/40 |
| 2005/0033214 A1* | 2/2005 | Cantor | A61F 13/0203 602/48 |
| 2007/0135777 A1* | 6/2007 | Greene | A61K 9/70 604/308 |
| 2009/0053273 A1 | 2/2009 | Le | |
| 2010/0263107 A1 | 10/2010 | Wang | |
| 2012/0061487 A1 | 3/2012 | Fortin | |
| 2012/0089103 A1 | 4/2012 | Tel-Ari | |
| 2012/0135448 A1 | 5/2012 | Parker et al. | |
| 2013/0012892 A1* | 1/2013 | Brown | A41D 27/00 604/290 |
| 2014/0052080 A1* | 2/2014 | Gibson | A61M 35/10 604/293 |
| 2017/0254005 A1 | 9/2017 | Gladish et al. | |
| 2019/0167535 A1 | 6/2019 | Hörle | |
| 2019/0307182 A1* | 10/2019 | Wiley | A61N 2/008 |

OTHER PUBLICATIONS

Examination Report in Australian Application No. 2021345259, mailed Apr. 18, 2024, 5 pages.

International Search Report and Written Opinion for PCT Application No. PCT/US2021/050839, mailed Dec. 17, 2021, 11 pages.

* cited by examiner

THERAPEUTIC WEARABLE ARTICLES

PRIORITY CLAIM

This application claims the benefit of and priority to PCT International Application No. PCT/US2021/050839, filed Sep. 17, 2021, which claims the benefit of and priority to U.S. Patent Application No. 63/081,115, filed Sep. 21, 2020, which applications are hereby incorporated by reference in their entireties as if fully set forth herein, for all purposes.

BACKGROUND

The inventive subject matter is generally directed to wearable articles with integrated delivery systems for the application of therapeutic, well-being or other treatments that therapeutically benefit the health or wellbeing of the wearer of the article (e.g., pharmaceutical, nutraceutical, aromatherapy).

Many compositions are known to provide therapeutic or well-being benefits when applied to the surface of the skin. Some act locally at the skin surface and others act transdermally. Often compositions are in a liquid or gel form. Transdermal applicators and other topical applicators that deliver a composition on to the skin are known. However, the prior art have shortcomings in the containment, application area and reusability of these treatments. Topical treatments that are applied directly to the skin by the wearer (like a cream or gel) can spread away from the targeted treatment area because they are not well-contained. These therapeutic treatments can unintentionally spread onto and be absorbed by the wearer's clothing or other surfaces with which the wearer may come in contact. This unintentional spreading de-concentrates the composition away from the targeted site, reducing the efficacy and longevity of the therapeutic treatment at the intended site of application. This unintentional spreading may also stain or mess the unintentionally contacted surfaces such as clothing, bedding and furniture. The treatments that are directly applied to the skin are difficult to apply by the wearer to such areas as the upper- and mid-back without the assistance of others. In the case of transdermal patches, the coverage area of each patch is limited, patches can be expensive, the patches are not reusable and pose a similar challenge as do topicals in that application onto areas such as the upper- and mid-back are extremely difficult without the assistance of others. Accordingly, there is substantial need for improvements in the application and management of compositions applied to the skin's surface for therapeutic or well-being effects.

SUMMARY

In certain embodiments, the inventive subject matter is directed to a wearable article, comprising a treatment delivery system, the system having a pliable assembly of layers, including an absorbent layer or other receptacle layer having a surface for absorbing or containing a treatment agent and intended to orient against a wearer's skin (dermal embodiment) or outside of the article oriented towards the wearer's olfactory system (aromatherapy embodiment); a base layer for the wearable article; a barrier or other backing layer for selectively blocking the passage of the treatment agent, while preferably allowing skin moisture to pass through the backing layer disposed between the receptacle layer and the backing layer.

In certain embodiments, the inventive subject matter is directed to a treatment delivery system for integration with a wearable article. The system includes a pliable assembly of layers, including a receptacle layer having a surface for containing a treatment agent and arranged to orient against a wearer's skin or outside the wearable article. A backing layer for selectively blocking the passage of the treatment is coupled with the receptacle layer, the delivery system being configured to map to a selected anatomical area and/or physiological system of an intended wearer; and wherein the receptacle layer's surface comprises a material selected from (1) knit or woven fibers, (2) hydrophilic fibers, or (3) spun superfine fibers or any combination thereof.

In certain embodiments, the inventive subject matter is directed to a wearable article that includes a treatment delivery system. The system includes a pliable assembly of coupled layers, including a receptacle layer having a surface for holding and/or absorbing a treatment agent and intended to orient against a wearer's skin or outside the article; a base layer; a backing layer for selectively blocking the passage of the treatment, the backing layer being disposed behind the receptacle layer and with the base layer; and wherein system is configured to map to a selected anatomical areas and/or physiological system of an intended wearer.

In any of the foregoing embodiments, the backing layer may be a membrane. The membrane may be a hydrophobic and/or a hydrophilic or oleophobic layer. The membrane may be one of many options in what is referred to as waterproof breathable fabrics include those composed of polyurethane-based fiber. The membrane may be made of superfine jet-extruded fibers.

In any of the foregoing embodiments, the receptacle layer may be hydrophilic and/or an oleophobic layer, which would be suitable for use with water-soluble treatment agents. The backing layer would therefore need to provide the appropriate repelling properties for such treatment agent and therefore may be hydrophobic.

In any of the foregoing embodiments, the treatment system may include a bonding section for bonding the system to a base layer of a wearable article, wherein the bonding section is disposed along at least one edge of the system, the bonding section being an adhesive or thermal bonding material or a stitchable edge.

In any of the foregoing embodiments, the receptacle layer may be a knit, woven, non-woven textile or any combination thereof.

In any of the foregoing embodiments, the wearable article may be a garment, sleeve or wrap. A sleeve or wrap may be configured for covering a selected area of the anatomy or physiology.

In any of the foregoing embodiments, the treatment system may map along the anatomical area and/or physiological pathway of the spine, neck, and/or back region.

In any of the foregoing embodiments, the system may map along an anatomical area and/or physiological pathway comprising a finger, wrist, hand and/or arm regions.

In any of the foregoing embodiments, the treatment system may map along an anatomical area and/or physiological pathway comprising hips, abdomen, buttocks and/or pelvic region.

In any of the foregoing embodiments, the treatment system may map along an anatomical area and/or physiological pathway comprising a shoulder, brachial plexus, collarbone and/or shoulder blade region.

In any of the foregoing embodiments, the treatment system may map along an anatomical area and/or physiological pathway comprising toes, ankle, foot, and leg regions.

In any of the foregoing embodiments, the treatment system may map along an anatomical area and/or physiological pathway comprising the skull and/or jaw region.

In any of the foregoing embodiments, the treatment system may be intended to be located on the outer side of the wearable item oriented so as to expose an applied treatment towards the wearer's olfactory system (olfactory embodiment)

In any of the foregoing embodiments, the backing layer may be breathable fabric like a Neoshell™ fabric from Polartec.

In any of the foregoing embodiments, the treatment system may further comprise a treatment agent applied to the receptacle layer.

In any of the foregoing embodiments, the waterproof rating of a layer, particularly the backing layer may be at least 5,000 mm.

In any of the foregoing embodiments, the breathability score (RET) of a layer, particularly the backing layer, may be 20 or less.

For the purposes of this patent, the term "treatment area" may include any skeletal, muscular, nervous, endocrine, cardiovascular, lymphatic, respiratory, digestive, urinary, reproductive or olfactory system.

The wearable articles are intended for repeated wear and may be washable, or they may be single-use disposable articles. The integrated delivery system 14 within each article may be detachable from the article and reusable. The same or different therapeutic agents may be applied again, and after use, the wearable article can be cleaned again creating a re-usable and sustainable pain management system or other therapeutic system. The integrated delivery system allows for the steady application of the treatment without adhesives or single- or limited-use patches providing a more environmentally friendly and sustainable solution. And the integrated delivery system allows the wearer to apply treatments to areas that would otherwise be very difficult to reach, such as between the shoulder blades.

These and other embodiments are described in more detail in the following detailed descriptions and the figures.

The following is a description of various inventive lines under the inventive subject matter. The appended claims, as originally filed in this document, or as subsequently amended, are hereby incorporated into this Summary section as if written directly in.

The foregoing is not intended to be an exhaustive list of embodiments and features of the inventive subject matter. Persons skilled in the art are capable of appreciating other embodiments and features from the following detailed description in conjunction with the drawings.

BRIEF DESCRIPTION OF THE DRAWINGS

The appended figures show embodiments according to the inventive subject matter.

DETAILED DESCRIPTION

Representative wearable articles in accordance with the inventive subject matter are illustrated in FIGS. 1-4 and described below. The wearable articles include traditional garments (FIG. 1-2), sleeves, and wraps (FIG. 3). For the purposes of this disclosure, "garment" is defined as typical clothing items (e.g., tops, bottoms, socks, gloves, pajamas, shorts, sweatshirt, tights.) For the purposes of this disclosure, a "sleeve" is defined as a one-piece article or tube-like structure that is pulled on and into place around the targeted treatment area (e.g., the elbow, forearm, knee, calf, and thigh). For the purposes of this disclosure, a "wrap" is defined as a long piece of material that is wrapped around the targeted treatment area (e.g., shoulder, back, hip and neck.)

Figure 4B:
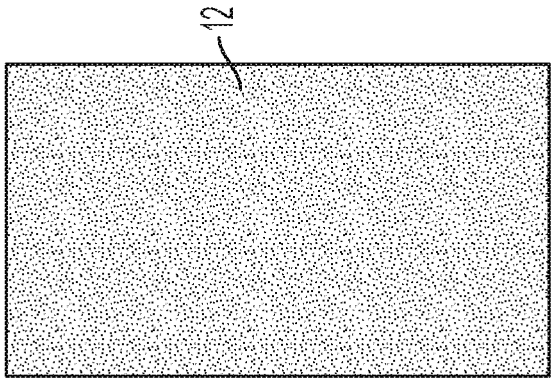
FIGS. 4A-B show plan views of assembled materials that may be incorporated in a wearable article, with FIG. 4A being a first side and FIG. 4*b* being an opposite second side.
Figure 4A:
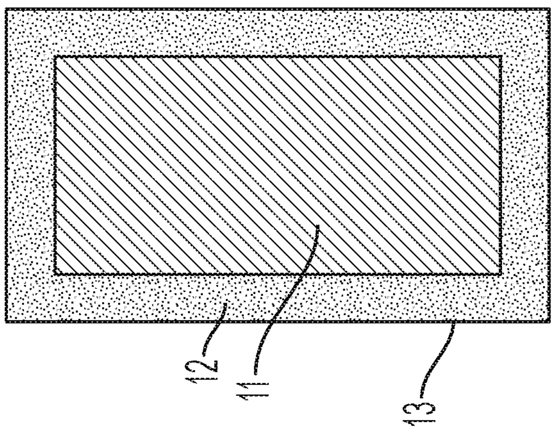

Each wearable article will have one or more than one or more portions with one or more integrated delivery systems 14. FIG. 4 shows the sample of the layered elements of an integrated delivery system 14. One purpose of the integrated delivery system is the containment of therapeutic treatment(s) so the treatment(s) may be targeted to the intended treatment area(s) or olfactory tissue. The integrated delivery system may be sized and shaped to map to desired areas of the anatomy or physiology, as discussed in more detail below. The system may be used with humans or animals.

For the purposes of this disclosure, the term "therapeutic treatment" will represent any healing, restorative, curing, or otherwise health or well-being beneficial compositions. Many of these therapeutic treatments are known to provide benefits when applied to the surface of the skin, delivered by transdermal action through the skin or inhaled through the olfactory system. For the purposes of this disclosure, the term "dermal" is defined as the application of a therapeutic treatment to the skin for action at the dermal layer, and the term "transdermal" is defined as the application of a therapeutic treatment to the skin where it is absorbed through the skin into the bloodstream, surrounding tissues and/or other physiological systems. The illustrated embodiments in the Figures are exemplary embodiments depict specific wearable articles, i.e., a t-shirt, long sleeve shirt, and a forearm sleeve. However, the inventive subject matter applies equally to any wearable article designed for a targeted treatment area that maps to an area of the human or animal anatomy and/or physiology.

Each article can be of any size to fit a child, adult, or animal application. In some embodiments, the shape may comfortably conform to the anatomical shape of the intended wearer to optimize treatment delivery either through skin contact for transdermal application and/or through the olfactory senses for aromatherapy application.

The main body of each article includes a base layer 10. The integrated delivery system 14 is a multi-layer system that includes layers 11 and 12, which are discussed in more detail below. One or more of the layers may, optionally, alone or in combination provide "thermophysiological" performance to the system and associated garments. Thermophysiological performance properties are aimed at managing heat and moisture transport for the system, to maintain a comfortable environment for the wearer in terms of optimized temperature and dryness during various level of activity.

In a dermal embodiment, i.e., an embodiment configured to contain a therapeutic agent and deliver it onto the skin of user and/or through the skin of a user transdermally, the integrated delivery system has one or more layers that are oriented towards the wearer's skin to optimize therapeutic treatment delivery from a layer having the therapeutic agent. For instance, layer 11 faces and contacts the user's skin. Layer 11 is adjacent the skin. Layer 12 is disposed behind layer 11 and may be attached to base layer 10 of the wearable article. Notably, the layers need not be separate and distinct layers in a laminate construction, they can be, for example, a monolithic construction where there is a bifurcation of materials or material properties as if there were two separate and distinct layers in a laminate construction. In other words, opposing surfaces of a laminate or monolithic construction are intended to have different surface properties (e.g., one side is a porous surface and the opposing side is relatively smooth surfaced, and/or one side is a hydrophilic surface and the other side is a hydrophobic surface).

In an aromatherapy embodiment, the integrated delivery system is oriented so that Layer 11 is oriented to the outside of the garment (away from the skin) and layer 12 is disposed behind layer 11 and attached to base layer 10 of the wearable article. It should be noted that aromatherapy treatments may be applied to either the aromatherapy embodiment or in combination with other treatments to the dermal embodiment.

In some embodiments, the wearable articles are intended for repeated wear. The integrated delivery system 14 within each article may be reusable. In such embodiments, after the wearable article has been worn, it can be cleaned and reused without appreciable degradation using traditional methods for washing and cleaning garments. The same or different therapeutic agents may be applied again, and after use, the wearable article can be cleaned again creating a re-usable and sustainable pain management system. The integrated delivery system allows for the steady application of the treatment without skin adhesives or single- or limited-use patches thereby providing a more environmentally friendly and sustainable solution. And the integrated delivery system allows the wearer to apply treatments to areas that would otherwise be very difficult to reach, such as between the shoulder blades.

Layers 11 and 12 may be classed according to their overall role in the integrated delivery system 14. The role of layer 11 in the integrated delivery system is essentially that of a receptacle that contains or holds a treatment agent(s). For the purposes of this disclosure, the term "receptacle" is defined as anything used to contain or hold a treatment agent. The role of layer 12 in the integrated delivery system is that of a backing layer. Layer 12 may serve to contain the treatment so that it does not seep into base layer 10 of the wearable, as well as to redirect the treatment back towards receptacle layer 11 to optimize concentration towards the targeted treatment area.

The layers of the integrated delivery system (layers 11 and 12) may be formed individually or together using weaving, knitting, spinning, or other fabrication methods. Surface treatments may be applied to layers, e.g., water resistance or waterproofing, stain resistance, antimicrobial resistance, etc. The layers can be assembled with commonly known techniques such as sewing, laminating, welding, thermal, or chemical bonding or fabricated together with such known techniques. A layer or layers may have a two- or three-dimensional form. A two-dimensional membrane is a planar or sheet form. A three-dimensional membrane may be a non-planar form, e.g., a cup shape. Three dimensional forms may be adapted to conform to selected, complementary shaped areas of anatomy, for example, a knee or elbow.

In some embodiments, a treatment delivery system 14 having receptacle layer 11 and backing layer 12 can include a bonding section for bonding the system to a base Layer 10 of a wearable article. The bonding section can be disposed, for instance, along at least one edge of the system or multiple edges, e.g., the entire perimeter. The bonding section is adapted to promote bonding, and, for example, can be a section having an adhesive (e.g., peel and stick), thermal bonding or other fusible material, or a stitchable edge.

As noted, receptacle layer 11 is the layer to which the treatment agent, e.g., a therapeutic or well-being agent is applied, and it is intended to go against the wearer's skin in the dermal embodiment or to be located on the outside of the wearable in an aromatherapy embodiment. In some embodiments, layer 11 is an receptacle layer, namely a layer having capacity to contain another substance, namely the treatment agent. For example, it could be a porous, matrix, sponge, cellular, or fiber or filament piled layer that has enhanced surface area for entrapping otherwise holding, and thereby containing the treatment agent.

As noted, the backing layer 12 may serve as a barrier or blocking layer that entirely or substantially prevents migration of the treatment through the layer. A backing layer that does not allow more than 30% of the treatment to migrate through to base layer 10 is considered to substantially prevent migration. In some embodiments, the barrier layer is sufficient to prevent less than 20%, 10%, 5%, 1% or 0.5% from migrating through to the base layer. In some embodiments, the backing layer may not need to block as much as 30% of the treatment from migration, but as long as it is under 50%, it will meet the requirement of substantially blocking.

In some embodiments, the backing or barrier layer 12 may be a fabric or membrane with any one or more of the following properties:

liquid repellency;
liquid resistance;
liquid imperviousness but with breathability;
liquid penetration resistance Various of these properties are discussed in more detail below.

The requirements and characteristics of the fabrics or other substrates for layers 11 depend on the types of treatment being contained by the receptacle layer. For example, the fabrics or other substrates may be optimized for containment, e.g., absorption of, the treatment agent and delivery to the intended anatomical or physiological system. As an example, a water-based treatment may require that layer 11 have hydrophilic (water attracting or absorbing) characteristics to best absorb or otherwise contain the treatment. Likewise, an additional example would be a treatment that is oil-based may require layer 11 fabrics or other substrates to have oleophilic or oil-attracting characteristics. In the case of treatments that are both water and oil containing, layer 11 would therefore need both hydrophilic and oleophilic absorbent or other containment capabilities. For instance, layer 11 can be fabric or other substrate formed with a mix of hydrophilic and oleophilic materials, like yarns or fibers. The yarns or fibers can be natural or synthetic or blends thereof. The requirements and characteristics of the fabrics or other substrates for layer 12 depend upon the types of treatment being applied to and absorbed by layer 11. In general, in contrast to layer 11's ability to absorb or otherwise, contain treatment agent, layer 12 may have opposite properties to repel the treatment agent. As an example, if the therapeutic treatment being applied to layer 11 is water-based or hydrophilic, the characteristics and requirements of layer 12 may be hydrophobic (water repelling) to provide the appropriate repelling properties. As an additional example, if the therapeutic treatment being applied to layer 11 is oil-based or oleophilic, the characteristics and requirements of layer 12 may be oleophobic (oil-repelling) to provide appropriate repelling properties. Layer 12 may also have the same hydrophilic or hydrophobic properties if it serves to physically block a selected treatment agent from passage through itself.

In another example, when the therapeutic treatment being applied to layer 11 has both water and oil properties (hydrophilic and oleophilic), the characteristics and requirements of layer 12 may be both hydrophobic and oleophobic to provide appropriate barrier properties. The layer 12 could have a mix of components to prevent migration of all component types in the treatment. For instance, layer 12 could have a mix of hydrophobic and oleophobic components and or structures, or it could be a laminate having a first sublayer of a hydrophobic component and a second sublayer of an oleophobic component.

Layers 11 and 12 may be classed according to their overall hydrophobicity/hydrophilicity based on the molecules making up a given layer or sublayer. In general, hydrophobic molecules have overall non-polar character. Similarly, in general, hydrophilic molecules have overall polar character. Water is a prime example of a polar or hydrophilic molecule. Oils and lipids are general examples of non-polar or hydrophobic molecules. The following terms, which are known in the art, may be used to indicate classes and subclasses of molecules:

- Non-Polar
  - Hydrophobic
    - Oleophilic
    - Lipophilic
- Polar
  - Hydrophilic
    - Oleophobic
    - Lipophobic Referring again to the receptacle layer 11, it can be a fabric having a hydrophobicity or hydrophilicity corresponding to the molecule type or types in the treatment agent. The general scientific principle is that like attracts like. Thereby, the polarity of layer 11 and the therapeutic treatment agent should be similar so that the receptacle layer attracts the treatment. For the backing Layer 12, the polarity of the materials in the substrate should be opposed to that of the treatment agent so that it repels the treatment thereby acting to contain the treatment to the receptacle layer and available to the targeted treatment area. If a treatment has a mix of hydrophobic and hydrophilic components, receptacle layer 11 can have a mix of like components. For instance, it can be a textile formed with a mix of hydrophobic and hydrophilic yarns. The yarns can be natural or synthetic or blends thereof. Likewise, the backing Layer 12 could have a mix of components to prevent migration of all component types in treatment. For instance, the backing layer could be a laminate having a first sublayer of a hydrophobic component and second sublayer of a hydrophilic component.

In some embodiments, the receptacle layer could be comprised of microfibers: While synthetic fibers by themselves may not absorb water the way natural cellulose fibers do, splitting them into microfibers creates pores and much more surface area between fibers. The microfiber textile structure is capable of absorbing water through capillary action among fine parallel fibers in the fabric. The absorbent characteristics can be varied with the splitting method used. Microfiber fabrics are also suited to absorbing dirt and grime along with moisture. Microfibers can be created or formed in woven, knits, and non-wovens, as person skilled in the art will appreciate.

The therapeutic or well-being agent (which may be simply referred to herein as the "treatment agent") may be any composition that is intended to provide perceived health or comfort benefits to the wearer such as but not limited to pharmaceuticals, nutraceuticals, homeopathic, herbal and aromatherapy compositions. These compositions can be of any suitable for topical and/or aromatherapy application. Examples of treatments include but are not limited to gels, creams, salves, essential oils, muscle treatments, cannabinoid applications, analgesics, anesthetics, pain medication, hormones, antihistamines, motion sickness medication, vitamins, nutraceuticals, and insect repellants. The treatment is applied to all or any part of the integrated delivery system typically prior to the item being applied to the wearer's body. In the dermal embodiment, the treatment may also be applied to the skin and then covered by the layer 11. In the dermal embodiment, when the wearable article is applied to the body, the treatment is delivered either through contact with the skin (dermal and transdermal) and/or through olfactory senses (aromatherapy). The treatment may have a non-liquid form when initially applied to the skin or to the layer 11. Or it may be in a more solid form like a gel or cream. In some cases, a more solid form may convert to a more liquid form, e.g., when exposed to body heat or an externally applied heat source or by physical rubbing (e.g., rupturing of liquid-containing microcapsules.)

When integrated delivery system 14 is integrated into a wearable article, it allows for sustained and continuous application of the treatment. The treatment may be applied to receptacle layer 11 in any manner that provides the ability to effectively deposit the therapeutic treatment onto layer 11*s*. Application methodologies may include but are not limited to spraying, mechanically rubbing, rolling on, or pouring on of the treatment.

For treatments with primarily water-soluble components, layer 12 may be a hydrophobic or waterproof material. In turn, layer 11 may be a hydrophilic layer designed to contain and deliver the treatment to the target area. This is just a non-limiting example. As indicated elsewhere in this disclosure, the material properties of layers 11 and 12 may vary based-upon the types of therapeutic treatments being considered for application. Layer 11 may be hydrophilic and/or hydrophobic (e.g., oleophilic) and therefore the fabric properties of layer 12 will be hydrophobic, (hydrophilic (e.g., oleophobic) or both to provide appropriate barrier functionality. Other variations are possible. For example, as indicated above and elsewhere herein, the ability of a layer to contain or to block a treatment or components may be independent of the hydrophobicity or hydrophilicity of its fibers. As an example, microfiber textiles are highly absorbent even though they are made of polyester and other non absorbent fibers.

Layer 12 may be affixed directly or indirectly to layer 11. Extending past the edges of layer 11, layer 12 is a more outward facing layer in the transdermal embodiment or more inward facing in the aromatherapy embodiment and layer 12 may directly or indirectly attach to the base layer 10 of the main wearable article. Base layer 10 may or may not be the outermost layer in the main wearable article. The integrated delivery system 14 may be attached to the layer 10 at the outermost edges 13 of layer 12.

The integrated delivery system 14 may be continuous or discontinuous depending upon the therapeutic goals and wearability requirements. Layer 11 may be continuous or discontinuous depending upon the design, therapeutic goals, and wearability requirements. In a continuous system over a given area, there is a generally uniform distribution of the layer material over a region of an article. In a discontinuous system, there is discrete patterning of material over a region of the article. For example, a region covering the back or arm of a user, for instance, could have a pattern of dots, parallel lines, or it could be a pattern that corresponds to and mimics an anatomical structure of bones, muscle, nerves, etc.

The fabrics, membranes, or other substrates used in the layers of the inventive subject matter may be selected to optimize body contact for treatment application, as well as wearer comfort so the article remains on the wearer. Comfort may include but is not limited to freedom of movement, breathability, anatomical conformity, and softness on skin contact.

For an article of clothing, base layer 10 may be of any appropriate material that provides desired attributes, e.g., comfort and conformity to the anatomical form, durability, thermal insulation, etc. Base layer 10 may be selected from textiles of natural fibers (including, but not limited to cotton, calico, hemp, bamboo, silk, wool, linen), synthetic fibers (including but not limited, to spandex, rayon, polyester, rayon, acrylic, olefin, Dacron, microfiber, Lycra,) or any suitable blends or combinations thereof. For a targeted treatment site wearable like the carpal tunnel hand and forearm wearable item (FIG. 3), base layer 10 may be made of elastic materials or construction to accommodate easy application and conforming wear.

Receptacle layer 11 may be of any material and/or substrate that provides the desired attribute of therapeutic treatment agent containment. The characteristics and requirements of the materials and substrates utilized in layer 11 may be dependent on the characteristics of the treatment agent (e.g., water or oil based). In an example of water-based treatments, the hydrophilic materials and/or substrates of layer 11 may be textiles consisting of natural fibers and natural fiber blends, other textiles that possess hydrophilic properties (microfibers, knits, woven and non-woven), hydrophilic membranes.

Breathability in layer 12 optionally may be selected as a desired feature. Breathability, a thermophysiological wear comfort factor, refers to the ability of a fabric to move heat vapor away from the body. Fabric breathability is desired for layer 12 to maintain the heat balance and dryness of the wearer's body during various level of activity. Breathability of the fabric is determined by the heat flow analysis from within the fabric to the exterior environment. By example, putting an article of clothing on starts to warm the body. As the body temperature rises, the body will produce sweat to regulate the microenvironment within the garment. This heat flow plays a significant role in maintaining thermophysiological comfort. Heat flow in porous media such as fabric is the study of energy movement in the form of heat. The heat flow is comprised of water (liquid) and air (gas), or basically the heat and sweat produced by the wearer when the fabric comes into contact with the wearers body. The transfer of heat occurs through the processes of convection, diffusion and/or radiation. Waterproof breathable (WBR) membranes, like GORE-TEX, are an example of common waterproof fabrics. These WBR fabrics are usually ePFTEs (expanded polytetrafluoroethylene). While waterproof breathable (WBR) membranes and coatings are often selected for their waterproof capabilities, the breathability of these fabrics is limited to the process of diffusion. Diffusion is dependent upon a concentration gradient to activate the heat flow. In the case of humidity (heat vapor), diffusion needs a difference in humidity on each side of the membrane in order for the fabric to move body heat and sweat. The bigger the difference, the higher the rate of diffusion. A fabric like Gore-Tex is most efficient when the wearer gets the wearable item to higher humidity levels inside the item for the "breathable" performance to kick in. Worn in a humid or warm environment, these fabrics are limited in their ability to move body sweat out of the garment—therefore less breathable and less comfortable for the wearer.

As indicated, to optimize comfort and extended period of comfortable wear, layer 12 fabrics optionally may be highly breathable (to move body heat and sweat away from the body), flexible to allow for freedom of movement and comfortable to the touch since part of the layer may be in contact with the wearer's body. This complex set of requirements is well served by products such as but not limited to spun films of superfine fibers like Polartec's NeoShell polyurethane fabric (www.polartec.com, Andover, Massachusetts, USA). Such fabrics also provides 4-way stretch and a soft and comfortable feel.

The waterproof or other barrier capabilities of layer 12 prevent the treatment applied to layer 11 from moving outside of the product, which may negatively result in product loss and/or potential staining of items that come into contact with the fabric (e.g., bedding, other clothing, furniture). Generally, backing layer properties can be made independent of the nature of the material properties of the material it is made of. For example, a barrier can be attained through a material that is non-porous and physically blocks liquid or other treatment phase from passing through the material regardless of the polarity of the materials.

In other cases, the backing layer need not be absolutely non-porous. For example, in the case of water soluble or polar treatments, a hydrophobic material or coating can help block transport of the treatment through the surface of layer 12, if the material has some porosity. Consider, for instance, knit or woven fabrics, which have inherent porosity. When such fabrics are treated oil-repellent finishes, e.g., fluorochemicals, the fabrics provide both oil resistance and water resistance or waterproofness. Oil-repellent fabric is therefore largely similar to waterproof fabric. This requires very low surface tension of the fabric. The use of fluorochemical polymers results in fabrics that are both highly water resistant and highly oil resistant by preventing the fibrous material from being wetted and soiled, by repelling aqueous and oily soil particles, and by preventing adhesion of dry soil through antiadhesive properties. Accordingly, in some embodiments, backing layer 12 can effectively block the passage of most any component type in a treatment while still having some porosity that allows for breathability to vent vapor, e.g., perspiration, from the skin side of delivery system 14. Accordingly, breathability in layer 12 may allow for aerobic air permeability and wicking capabilities to keep moisture vapor moving away from the wearer's core thereby increasing comfort.

The inventive subject matter contemplates that layer 12 can be formed from any of various backing material known to persons skilled in the art, including:

1. Closely woven fabrics
2. Microporous and monolithic membranes and coatings
3. Hydrophobic membranes and coatings 4. Combination of microporous and hydrophilic membranes and coating
5. Retroreflective microbeads
6. Smart breathable fabrics
7. Fabrics based on biomimetics For waterproof or resistant barrier layers, the following is an outerwear waterproofness rating scale that has been used in the outerwear industry.

| 8. Waterproof Rating (mm) | Level of Water Resistance |
|---|---|
| 0-5,000 mm | No resistance/Little resistance |
| 6,000-10,000 mm | Some resistance. Rainproof and waterproof under light pressure |
| 11,000-15,000 mm | Normal resistance. Rainproof and waterproof except under high pressure. |
| 16,000-20,000 mm | High resistance. Rainproof and waterproof under high pressure. |
| 20,000 mm+ | Highest resistance |

The following is an outerwear breathability rating scale that has been used in the outerwear industry, which may be used to assess and rate backing layer 12.

| RET Score | Breathability Notes |
|---|---|
| 0-6 | Extremely breathable. Comfortable at higher activity rate. |
| 6-13 | Good to very good breathability. Comfortable at moderate activity rate. |
| 13-20 | Satisfactory to acceptable breathability. Uncomfortable at high activity rate. |
| 20-30 | Unsatisfactory or slightly breathable. Moderate comfort at low activity rate. |
| 30+ | Unsatisfactory or not breathable. Uncomfortable and short tolerance time. |

A wide variety of materials (synthetic, natural, bio-based-plants, bio-based-fermented) and fabric/substrate types (knits, wovens, and nonwovens) are contemplated for use in end products. In some embodiments, any one or more layers of an integrated system of layers 11 and 12 may be textile made of superfine fibers. Non-limiting examples of superfine fibers that may be created using methods and apparatuses as discussed herein include natural and synthetic polymers, polymer blends, and other fiber-forming materials. Polymers and other fiber-forming materials may include biomaterials (e.g., biodegradable and bioreabsorbable materials, plant-based biopolymers, bio-based fermented polymers), metals, metallic alloys, ceramics, composites and carbon superfine fibers. Non-limiting examples of specific superfine fibers made using methods and apparatuses as discussed herein include polytetrafluoroethlyene (PTFE) polypropylene (PP), polyurethanes (PU), Polylactic acid (PLA), nylon, bismuth, and beta-lactam superfine fibers.

Suitable films/membranes and fabrics are commercially available to satisfy a range of desired barrier properties (e.g., waterproofness) and breathability ratings, including any combination of ratings from the tables above. Some such films and fabrics are identified below.

Traditionally, one of leading forms of wearable waterproof fabric membranes is thermo-mechanically expanded polytetrafluoroethylene or other fluoropolymers, including, but not limited to perfluoroalkoxy polymer, fluorinated ethylene-propylene, polyvinylfluoride, polyethylenetetrafluoroethylene, polyethylenechlorotrifluoroethylene, and polyvinylidene fluoride. This family of fabrics is referred to as ePTFEs. An expanded polytetra-flouroethylene membrane is created when PTFE—a linear polymer consisting of fluorine and carbon molecules—is expanded, creating a microporous structure. These waterproof breathable (WBR) membranes are commercially available and include the trademark GORE-TEX® of W.L. Gore & Associates, Inc.

While WBRs provide exceptional hydrophobicity and waterproof, they have less than ideal breathability, and are stiff and often noisy to the wearer. These characteristics result in lower thermophysiological wear comfort and while suitable for use in layer 12, they may not be ideal for all application. Accordingly, the inventive subject matter is also directed to other classes of fabrics that allow for greater thermophysiological wear comfort for layer 12.

Newer barrier membranes, which include waterproofness and possibly oil resistance as well, allow for greater breathability than traditional ePTFE's like GORE-TEX. Polartec NeoShell film (microporous polyurethane), eVent membranes (modified ePTFE), (www.eventfabrics.com) OutDry membranes (www.columbia.com/technology-outdry) and Mountain hardware DryQ (www.mountainhardwear.com) maintain waterproofness and improve breathability and air permeability. These products generally focus on improving breathability and heat flow by providing convection heat transfers capabilities in addition to the diffusion heat transfer found in ePTFEs. These waterproof convective materials breathe significantly better than their non-convective counterparts, and, therefore, like materials are a suitable choice for layer 12.

An example of an appropriate fabric for layer 12 is a microporous polyurethane-based fabric like Polartec's NeoShell™. Such polyurethane fabrics are not only waterproof, but they are also oleophobic, and more permeable to allow for improved level of breathability and temperature management. Microporous polyurethane fabric also has a 4-way stretch and softer fabric feel. As described in more detail below, the membrane may be formed using micro- or nanoscale jet extrusion methods like electrospinning. The high permeability of the waterproof membrane provides greater thermophysiological wear comfort with wicking capabilities to transport moisture vapor away from the skin.

The air permeability of microporous polyurethane allows for two forms of heat transfer: convection and diffusion. Unlike diffusion that relies and gradient differentials, convection moves air directly through the membrane. If the air vapor starts at a constant temperature and the surface of the body starts to increase in temperature above that of the air vapor, there will be convective heat transfer from the body surface to the air vapor. This heat transfer to the vapor actively moves the air vapor through the fabric. Fabrics with the ability to move air vapor through both diffusion and convection produce higher breathability and wearer comfort and may be the preferred selection for layer 12.

Physiological wear comfort also encompasses fabric feel and freedom of movement and is important in the selection of the fabrics for layer 12. While producing high waterproof ratings, ePTFE membranes tend to also be noisy and stiff with minimal stretch which also reduces wearer comfort.

Advances in textile processing technologies discussed above are also producing fabrics that are not only breathable and waterproof but also stretchable and soft to the touch. Fabric stretchability provides freedom of movement and wearer comfort as the conduct daily activities and routines, including sleep. This stretchability also allows for article to be incorporated into designs that comfortably conform to the wearer's body to promote the contact of the article with wearer skin and body. Because layer 12 comes into direct contact with the wearer's body, fabrics softness enhances thermophysiological wear comfort which promotes the wearer ability to wear the article for sustained periods of time to optimize treatment delivery. Fabrics with such wear comfort of stretchability and softness are particularly suited for layer 12.

In some embodiments, backing layer 12, which serves as a blocking layer, is formed as a two- or three-dimensional webs, i.e., mats, films or membranes.

In some embodiments, the fibers for backing layer 12 may be produced using forced ejection of a selected starting fiber-forming, fluid material through an outlet port, e.g., a nozzle with fine openings. The outlet port is configured with a size and shape to cause a fine jet of the fluid material to form on exit from the outlet port. As used herein, an outlet port means an exit orifice plus any associated channel or passage feeding the outlet port and serving to define the nature of the expelled jet of fiber-forming material. Due to factors such as surface tension, fluid viscosity, solvent volatility, rotational speed, and others, the ejected material can solidify as a fiber that may have a diameter that is significantly less than the inner diameter of the outlet port. Herein, such expulsion of flowable material from an outlet port as a jet that solidifies as a fiber may be referred to as "jet extrusion".

The jet of expelled material is directed to a collector, i.e., any targeted substrate, where it is gathered for use in an end product or as the end product or an intermediate to an end product. The collected fiber material forms a web of two- or three-dimensional entangled fibers that can be worked to a desired surface area and thickness, depending on the amount of time fibers continue to be expelled onto a collector, and control over the surface area of the collector (e.g., a moving belt as a collector can allow for sheets of material of unlimited length). Other properties, such as web density and porosity will depend on such factors as the nature of the fibers, processing temperatures, speed, and path of jets, etc. The working of the web to a desired thickness, surface area, density, and/or porosity may also include post-processing steps, such as compression of the collected webs, thermal processing for densification or expansion (depending on nature of fibers), chemical processing, and processing with electromagnetic radiation (e.g., UV wavelengths to induce cross-linking).

In certain embodiments, a rotary device imparts centrifugal force on a fiber-forming material to cause jet extrusion and consequently fiber formation. The force that is imparted on the source material may come from various systems and techniques that may or may not require applied electrical fields, as in electrospinning. For example, U.S. Pat. Nos. 4,937,020, 5,114,631, 6,824,372, 7,655,175, 7,857,608, 8,231,378, 8,425,810, and US Publication No. 20120135448, teach various devices and processes for forced ejection of fiber-forming material through an outlet port on a rotary device. The foregoing collection of patent documents includes disclosures for systems for production of fibers with average diameters in the micron-scale or nanoscale range. The foregoing patent documents are hereby incorporated in their entireties for all purposes. An alternative approach to rotary systems is based on non-rotary pressure feeding of a fiber-forming fluid through an outlet port that creates a jet of the fluid that forms into a fiber. For example, U.S. Pat. No. 6,824,372, which is hereby incorporated by reference in its entirety for all purposes, discloses a chamber that imparts ejection force on a fiber-forming fluid contained therein via oscillating pressure changes that are generated by a movable wall for the chamber.

In some embodiments, the inventive subject matter relates to compositions of nonwoven, fibrous films or membranes based on superfine fibers for use in construction of the inventive articles contemplated in this disclosure. As used herein, superfine fibers means fibers having an average diameter (or other major cross-sectional dimension in the case of non-circular fibers) in the micron scale to nanoscale. As used herein, "micron scale" means the fibers have average diameters in the range of single-digit microns to as low as about 1000 nanometers. In the textile industry, nanoscale fibers have average diameters in the range of about 100-1000 nanometers or less). In certain embodiments, superfine fibers exhibit a high aspect ratio (length/diameter) of at least 100 or higher. Superfine fibers may be analyzed via any means known to those of skill in the art. For example, Scanning Electron Microscopy (SEM) may be used to measure dimensions of a given fiber.

Electrospinning and forcespinning are known processes to extrude super fine fibers using jet expulsion under electric fields or centrifugal force to elongate the fibers. This creates cohesive, nonwoven mats of fiber networks. Fiber crossings generate contact points. This creates inter-fiber porosity, and, in the case of relatively long fibers, intra-fiber porosity, as well. Fiber contacts and fiber morphology influence the size of the pores. Because of the network structure, these pores exist in multiple planes (vertically, horizontally, and diagonally).

In electrospun or forcespun membranes, pore sizes as small of 500 nm have been recorded. Water vapor molecules are approximately 0.4 nm, and water molecules (liquid) are approximately 500,000 nm. This allows vapor to pass through electrospun membranes but not water in the liquid form. In certain embodiments using forcespining, a rotating element is rotated within a range of about 500 to about 100,000 RPM. In certain embodiments, the rotation during which material is ejected is at least 5,000 RPM. In other embodiments, it is at least 10,000 RPM. In other embodiments, it is at least 25,000 RPM. In other embodiments, it is at least 50,000 RPM. During rotation, a selected material, for example a polymer melt or polymer solution, is ejected as a jet of material 15 from one or more outlet ports 16 on the spinneret into the surrounding atmosphere. The outward radial centrifugal force stretches the polymer jet as it is projected away from the outlet port, and the jet travels in a curled trajectory due to rotation-dependent inertia. Stretching of the extruded polymer jet is believed to be important in reducing jet diameter over the distance from the nozzle to a collector. The ejected material is expected to solidify into a superfine fiber by the time it reaches a collector. The system includes a collector for collecting the fiber in a desired manner. For example, the fibers could be ejected from the spinneret onto a surface disposed below the spinneret or on a wall across from outlet ports on the spinneret. The collecting surface could be static or movable. To form a sheet or mat of fibrous material, the surface could be a flat surface. The flat surface could be static or movable.

A movable flat surface could be part of a continuous belt system that feeds the fibrous material into rolls or into other processing systems. Another processing system could be an in-line lamination or material deposition system for laminating or depositing other materials onto sheet material produced using the force-spinning system or other system for producing sheeted material of superfine fibers. In other embodiments, the flat surface could support a layer of another material onto which the fibers are deposited. For example, the layer of materials onto which fibers are deposited could be an inner or outer layer for a composite assembly of layers for an end product, such as an item of apparel.

In certain embodiments, the collecting surface is a 3D object such as a mold or 3D component of an end product.

To direct fibers to a desired collecting surface (a "collector"), a fiber-directing system may be made a part of the force-spinning system. For example, the directional system may be configured to provide air from above and/or vacuum from below the desired collector to direct the fibers to the collector.

As the superfine fibers are laid upon each other in electrospinning or forcespinning, contacts points are made at intersections, and the fiber constituents bind together in a web or other desired form of intersecting or entangled fibers. If any web-bonding of the contact points is desired, it may be accomplished via application of heat (thermal bonding), heat and pressure, and/or chemical bonding. The spinning system may include heating elements, pressure applicators, and chemical bonding units for achieving such bonding.

The membranes may be directly spun onto the chosen face fabric of a desired material, e.g., layers 10 and/or 11, or the membranes may be spun onto contact paper and then laminated onto the chosen face fabric of the final material. The membrane, either deposited directly on the fabric, or material, or laminated on the material. The diameter of the nanofiber affects pore size of the membrane. The cross-sectional morphology of the fibers and fiber thickness affect the surface area of the fibers. Increasing the surface area of the fibers can reduce the pore size. Reducing the fiber diameter is a way to increase surface area/volume ratio. Therefore, fiber diameter is a way to control thickness, durability, and moisture vapor transfer. Thickness affects weight of the membrane. Collectively, these factors influence the blocking (e.g., waterproofness) and the breathability of the membrane, and the durability of the membrane.

Where desired, nanofiber diameters according to the inventive subject matter can be anywhere in the nanoscale range. A suitable range for applications described herein is believed to be about 100 nm to about 1000 nm. Pore size influences air permeability. Therefore, the air permeability for a membrane may be controlled for most applications using nanofibers in the foregoing size range. Fiber-forming materials of use for softshell and waterproof breathable applications include PFTE dispersions, polyurethanes, nylons, polyesters, bio-based materials, e.g., such cellulosic materials, silk proteins, and other fiber-forming materials that are to be discovered, including other polymers derived from natural and synthetic sources.

In certain embodiments of the inventive subject matter, the flowable, fiber-forming material may be a mixture of two or more polymers and/or two or more copolymers. In other embodiments, the fiber-forming material polymers may be a mixture of one or more polymers and or more copolymers. In other embodiments, the fiber-forming material may be a mixture of one or more synthetic polymers and one or more naturally occurring polymers.

In some embodiments according to the inventive subject matter, the fiber-forming material is fed into a reservoir as a polymer solution, i.e., a polymer dissolved in an appropriate solution. In this embodiment, the methods may further comprise dissolving the polymer in a solvent prior to feeding the polymer into the reservoir. In other embodiments, the polymer is fed into the reservoir as a polymer melt. In such embodiment, the reservoir is heated at a temperature suitable for melting the polymer, e.g., is heated at a temperature of about 100° C. to about 300° C.

In some embodiments according to the inventive subject matter, a plurality of micron, submicron or nanometer dimension polymeric fibers are formed. The plurality of micron, submicron or nanometer dimension polymeric fibers may be of the same diameter or of different diameters.

In some embodiments according to the inventive subject matter, the methods of the invention result in the fabrication of micron, submicron, or nanometer dimensions. For example, it is believed possible to fabricate polymeric fibers having diameters (or similar cross-sectional dimension for non-circular shapes) of about 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 nanometers, or 2, 5, 10, 20, 30, 40, or about 50 micrometers. Sizes and ranges intermediate to the recited diameters are also part of the inventive subject matter.

The polymeric fibers formed using the methods and devices of the invention may be of a range of lengths based on aspect ratios of at least 100, 500, 1000, 5000 or higher relative to the foregoing fiber diameters. In one embodiment, the length of the polymeric fibers is dependent at least in part, on the length of time the device is rotated or oscillated and/or the amount of polymer fed into the system. For example, it is believed that the polymeric fibers may be formed having lengths of at least 0.5 micrometer, including lengths in the range of about 0.5 micrometers to 10 meters, or more. Additionally, the polymeric fibers may be cut to a desired length using any suitable instrument. Sizes and ranges intermediate to the recited lengths are also part of the inventive subject matter.

As used herein, the terms "fiber" and "filaments" may be used interchangeably, with the term "filament" generally referring to a category of "fiber" of high aspect ratio, e.g., a fiber of relatively long or continuous lengths that can be spooled around a desired object. Further, synthetic fibers are generally produced as long, continuous filaments. In contrast, "staple fibers" usually refers to natural fibers, which tend to be relatively short because that is how they are typically grown. Long synthetic filaments can be chopped into short staple fibers. In summation, a filament is a fiber, but a fiber can be in different lengths (staple or long or continuous).

In some embodiments, the polymeric fibers formed according to the methods of the inventive subject matter are further contacted with or exposed to an agent to reduce or increase the size of pores, or the number of pores, per surface unit area in the polymeric fibers. For example, various known chemical agents may be used, which are known to increase or decrease cross-linking in polymers or denature non-covalent linkages. Non-chemical agents may include heat and electromagnetic radiation.

The inventive subject matter is particularly suited for producing end-products having component layers with waterproof and breathable protection. Other nanofiber webs for waterproof and moisture breathability have been produced via electrospinning. Similar dimensions are believed possible by jet extrusion, but with greater fiber lengths than possible via electrospinning. The dimensions of these are 1000 nm or less. The webs are expected to have a range of fabric weights and weigh about 5 to about 25 $g/m^2$, with a thickness of about 10 to about 50 micrometers (See, e.g., Korean Patent Document No. 20090129063 A). For forcespun microporous membranes for waterproof/breathable applications, PTFE is an example of a suitable fiber-forming material. Suitable PTFE fiber diameters may range from about 100 nm to about 1000 nm. A range of thicknesses of webs is possible. A suitable thickness of the membrane thickness may be from about 7 micrometers to about 50 micrometers. A range of pore sizes in webs is possible. Suitable pore sizes for waterproof/breathable applications include about 250 nm or greater.

Superfine fiber collections may include a blending of multiple materials, as indicated above. In certain embodiments, fibrous webs of the present disclosure may include elastic fibers, such as elastane, polyurethane, and polyacrylate based polymers, to impart stretchability to the nonwoven textiles made according to the inventive subject matter.

Figure 1A:
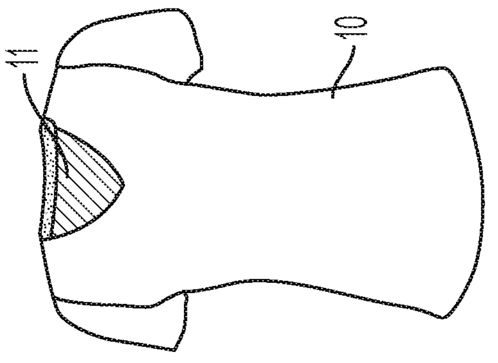
FIGS. 1A-C show front exterior (1A), rear exterior (1B) and rear interior (1C) views of an article of clothing, namely a shirt.
Figure 1B:
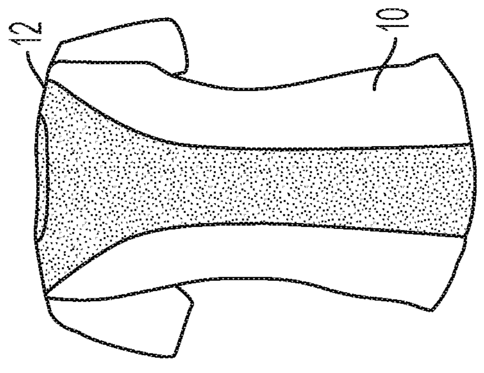
Figure 1C:
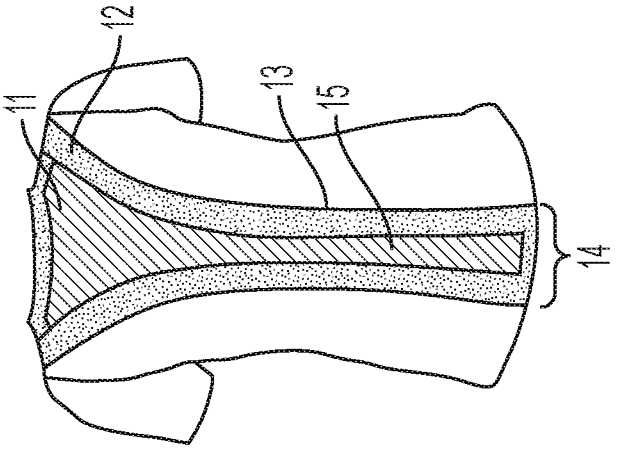
Figure 2A:
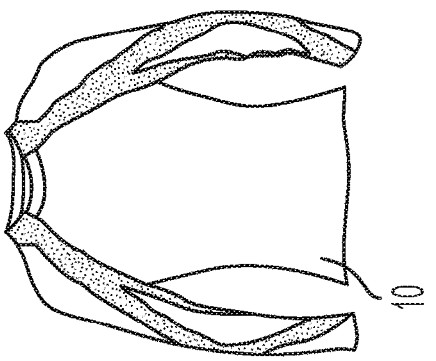
FIGS. 2A-D show front exterior (2A), front interior (2B) rear exterior (2C) and rear interior (2D) views of another article of clothing, namely a shirt.
Figure 2B:
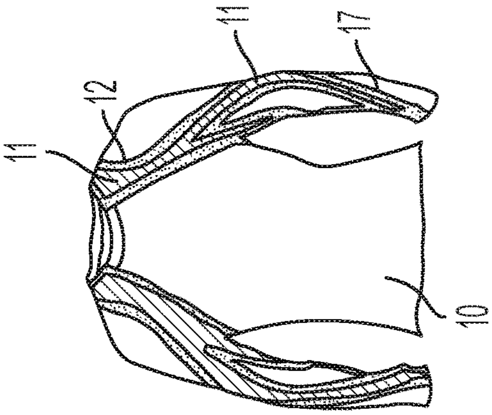
Figure 2C:
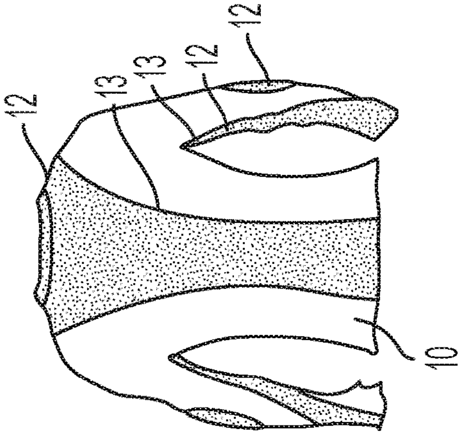
Figure 2D:
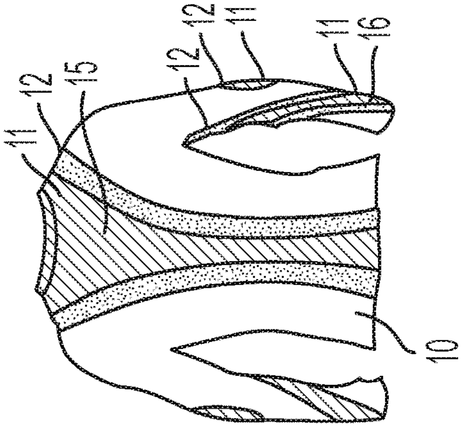
Figure 3A:
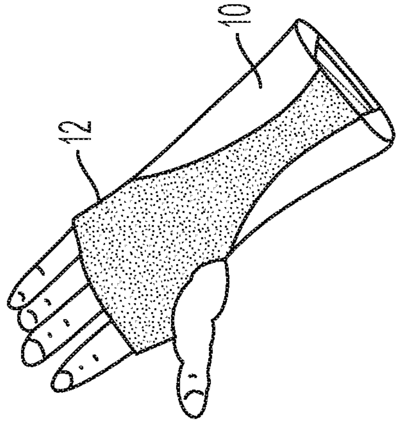
FIGS. 3A-D show perspective views of a wearable article for covering areas of wearer's hand, wrist and forearm, with FIGS. 3A-B being respectively posterior sides of the outside and inside of the article, and FIGS. 3C-D being respectively anterior sides of the outside and inside of the article.
Figure 3B:
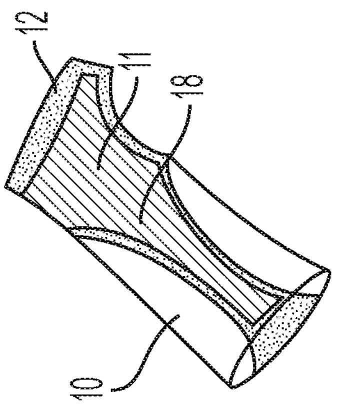
Figure 3C:
Figure 3D:
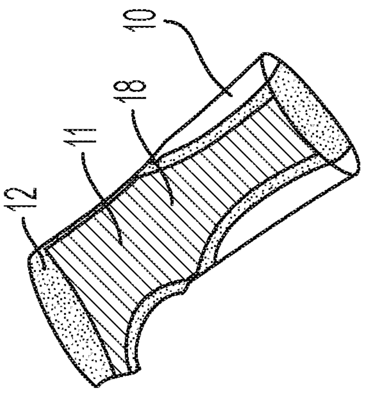

Each wearable item may be designed with specific therapeutic intentions, including but not limited to the treatment of pain, inflammation, and muscle tension. The integrated delivery system 14 of each wearable is designed to help achieve therapeutic goals by targeting underlying and associated anatomical and physiological systems, areas, and pathways. These anatomical and physiological systems, areas and pathways may include but are not limited to the skeletal, muscular, nervous, endocrine, cardiovascular, lymphatic, respiratory, digestive, urinary, reproductive, or olfactory system. As an example, in FIG. 1, the therapeutic goal of the wearable t-shirt is to mitigate neck and back pain. Skeletal, nerve and musculature distress along and associated with the spinal column significantly contribute to back and neck pain. Therefore, the integrated delivery system 14 in FIGS. 1B and 1C is designed to target a therapeutic treatment along the spinal column (central nervous system) 15 with the therapeutic goal of back pain, neck pain, and muscle tension relief.

Each wearable may have one or more than one therapeutic goal. The wearable article will have one or more than one integrated delivery systems 14 to target the relevant anatomical and physiological areas, pathways and systems associated with the therapeutic goals. As an example, FIG. 1 depicts a single integrated therapeutic pathway 14 to alleviate neck and back pain, muscle tension and inflammation by targeting the spinal column pathway 15 for therapeutic treatment delivery. In FIG. 2, an example is provided of a wearable article with multiple therapeutic goals. Hand, elbow, shoulder and arm pain, muscle tension and inflammation may be the result of various injuries and disturbance along the nervous system pathways from the cervical neck region, through the brachial plexus and down the arm via the ulnar and radial nerves. The wearable in FIG. 2 depicts three integrated delivery systems to support these complex pain regions and therapeutic goals. In FIGS. 2A-2D, the integrated delivery system pathway 16 follows the ulnar nerve from the pinky region of the hand up the inside elbow and to the front of the brachial plexus region (near the collarbone). The integrated delivery system pathway 17 follows the radial nerve pathway from the thumb region to the outside elbow and to the front of the brachial plexus region. These two integrated delivery systems are then integrated with the integrated delivery system pathway 15 that follows the spinal column allowing treatment in particular for the cervical neck region where the ulnar and radial nerves attach. FIG. 3 provides an example of a wearable targeted to a specific treatment area. In this example, the therapeutic goal is to treat carpal tunnel pain that is caused by medial nerve compression. The integrated delivery system 14 targets treatment to the medial nerve pathway 18 on both the posterior (top) side (FIGS. 3A and 3B) and anterior (palm) side (FIGS. 3C and 3D) of the hand and wrist.

Figure 5B:
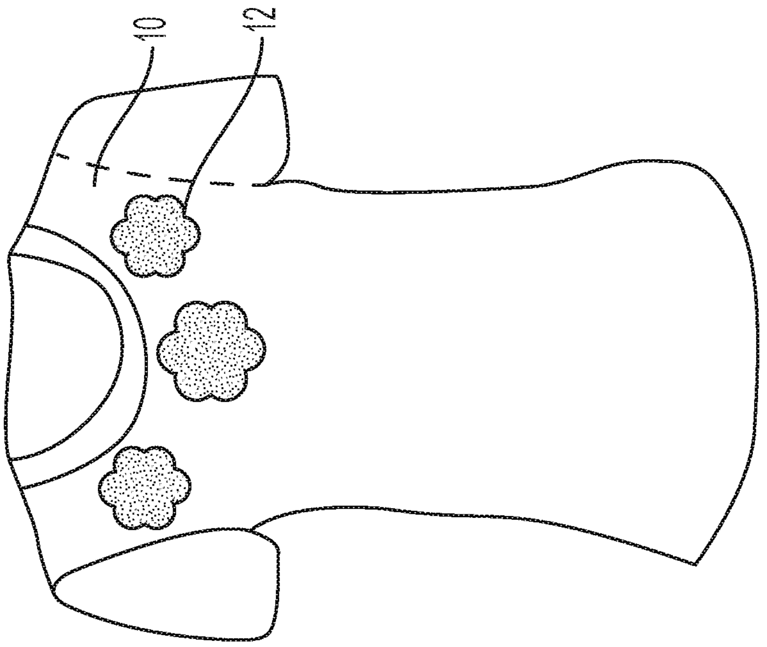
FIGS. 5A-5B show front views of yet another article of clothing, namely a shirt, with FIG. 5A being an exterior view and FIG. 5B being an interior view.
Figure 5A:
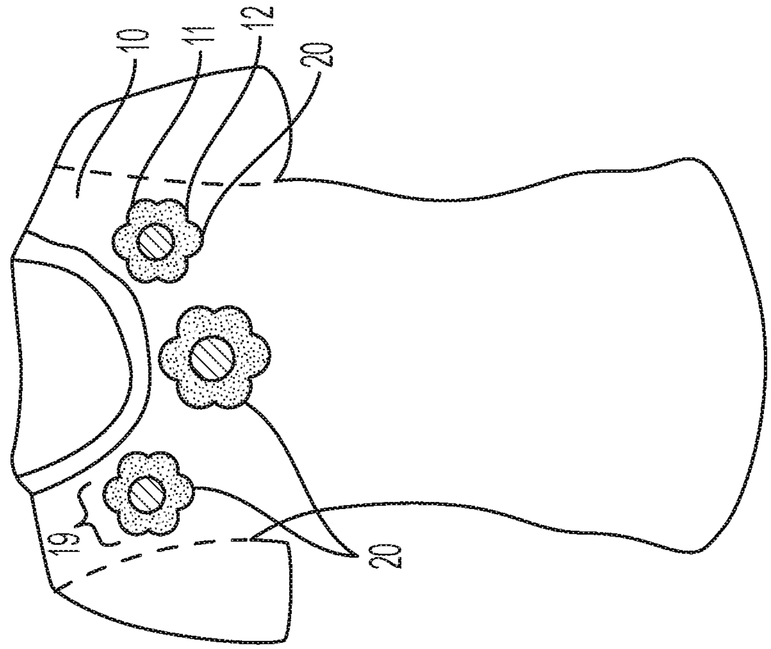

FIG. 5 provides an example of both an aromatherapy embodiment as well as a discontinuous integrated delivery system embodiment. In this example, the therapeutic goal is to deliver aromatherapy. The integrated delivery system pathway 19 is positioned to the outside of the wearable item and towards the wearer's olfactory system (FIG. 5A). In FIGS. 5A and 5B, three integrated delivery systems 20 are depicted on the single wearable providing an example of a discontinuous embodiment. FIG. 5B depicts backing layer 12 positioned in an inward embodiment.

The foregoing pathways are non-limiting and persons skilled in the art may use the principles disclosed herein to direct treatments to any anatomical region and/or physiological system or definable pathway, including but not limited to desired central or peripheral nervous system pathways (e.g., the spinal column); along muscles and their associated connective tissues; the abdominal region and its muscles, systems or organs; tendons; ligaments; over acupuncture, acupressure or Chakra points or lines; bone or associated groups of bones defining anatomical features (e.g., wrist, forearm, elbow, upper arm, pelvis, hips, ribs, shoulder, brachial plexus, collarbone, shoulder blades, toes, foot, ankle, calf, knee, thigh, toes hands fingers, spinal column, including neck, skull, jaw, etc.); body organs, including the heart, lungs, kidney, liver, pancreas, brain, olfactory system etc. The pathway may also be defined to correspond to any physiological process occurring in the body with the integrated system mapping to all or selected components of the anatomy involved in the physiological process.

The treatment that is applied to layer 11 of the integrated delivery system 14, may be applied to all or part of layer 11 depending on the wearer's therapeutic goals. As the innermost layer of the wearable article in the dermal/transdermal embodiment, layer 11, when in direct contact with the wearer's skin, delivers the continuous and extended application of the treatment. In the example of the t-shirt in FIG. 1, the treatment can be delivered continuously throughout the day or night when the item is worn. And, because the treatment is contained in layer 11 and is prevented from unintentionally moving out the back of layer 11 or onto the base layer 10 by the backing and barrier properties of Layer 12, there is minimized treatment waste and optimized concentrated treatment to the targeted areas.

Persons skilled in the art will recognize that many modifications and variations are possible in the details, materials, and arrangements of the parts and actions which have been described and illustrated in order to explain the nature of the inventive subject matter, and that such modifications and variations do not depart from the spirit and scope of the teachings and claims contained therein.

All patent and non-patent literature cited herein is hereby incorporated by references in its entirety for all purposes.

As used herein, "and/or" means "and" or "or", as well as "and" and "or." Moreover, any and all patent and non-patent literature cited herein is hereby incorporated by references in its entirety for all purposes.

The principles described above in connection with any particular example can be combined with the principles described in connection with any one or more of the other examples. Accordingly, this detailed description shall not be construed in a limiting sense, and following a review of this disclosure, those of ordinary skill in the art will appreciate the wide variety of systems that can be devised using the various concepts described herein. Moreover, those of ordinary skill in the art will appreciate that the exemplary embodiments disclosed herein can be adapted to various configurations without departing from the disclosed principles.

The previous description of the disclosed embodiments is provided to enable any person skilled in the art to make or use the disclosed innovations. Various modifications to those embodiments will be readily apparent to those skilled in the art, and the generic principles defined herein may be applied to other embodiments without departing from the spirit or scope of this disclosure. Thus, the claimed inventions are not intended to be limited to the embodiments shown herein but are to be accorded the full scope consistent with the language of the claims, wherein reference to an element in the singular, such as by use of the article "a" or "an" is not intended to mean "one and only one" unless specifically so stated, but rather "one or more".

All structural and functional equivalents to the elements of the various embodiments described throughout the disclosure that are known or later come to be known to those of ordinary skill in the art are intended to be encompassed by the features described and claimed herein. Moreover, nothing disclosed herein is intended to be dedicated to the public regardless of whether such disclosure is explicitly recited in the claims. No claim element is to be construed as "a means plus function" claim under US patent law, unless the element is expressly recited using the phrase "means for" or "step for".

The invention claimed is:

1. A treatment delivery system for integration with a wearable article, the system including a pliable assembly of layers, comprising: a receptacle layer having a surface for containing a treatment agent and arranged to orient against the skin of an intended wearer or outside the wearable article, and wherein the treatment agent includes at least one of pharmaceuticals, nutraceuticals, homeopathic, herbal treatment agent; a coupled backing layer with a waterproof rating of at least 5,000 millimeters (mm) and a breathability score (RET) of 20 or less that allows less than 30% of the treatment agent to migrate through the backing layer; the delivery system being shaped and configured to correspond to and mimic a predetermined nervous system pathway of the intended wearer and to deliver the treatment agent to the intended wearer's skin along the pathway to provide a transdermal delivery and therapeutic effect; wherein the treatment delivery system includes a bonding section for bonding and integrating the treatment delivery system to a selected portion of the wearable article that maps to the predetermined nervous system pathway, and wherein the bonding section is disposed along at least one edge of the system and comprises an adhesive, chemical or thermal bonding material; and wherein the assembly of layers form a discrete element that is integratable with a base layer of the wearable article by the bonding section in a manner that the backing layer is disposed between the receptacle layer and the base layer.

2. The treatment delivery system of claim 1, wherein the backing layer comprises a microporous polyurethane-based fabric that is waterproof and oleophobic.

3. The treatment delivery system of claim 1, wherein the treatment delivery system further comprises a treatment agent applied to the receptacle layer.

4. The treatment delivery system of claim 1, wherein the backing layer extends past the edges of the receptacle layer.

5. The treatment delivery system of claim 1, wherein the backing layer is disposed as an intermediate layer between the receptacle layer and a base layer.

6. A wearable article, comprising a plurality of discontinuous and discrete treatment delivery systems, each system including, a pliable assembly of layers, comprising: a receptacle layer having a surface for containing a treatment agent and arranged to orient against a wearer's skin or outside the article, and wherein the treatment agent includes at least one of pharmaceuticals, nutraceuticals, homeopathic, herbal treatment agents; a base layer; a backing layer with a waterproof rating of at least 5,000 millimeters (mm) and a breathability score (RET) of 20 or less that allows less than 30% of the treatment agent to migrate through the backing layer to the base layer, and wherein the each system is configured within a selected portion of the wearable article and shaped to correspond to and mimics a predetermined nervous system pathway of an intended wearer that is different from that of any other of the treatment systems, and wherein each system is configured to deliver the treatment agent to the intended wearer's skin along the predetermined nervous system pathway to provide a transdermal delivery and therapeutic effect.

7. The wearable article of claim 6, wherein the backing layer comprises a membrane that blocks passage of a fluid treatment agent under a Waterproof rating of 10,000 mm or higher.

8. The wearable article of claim 6, wherein the membrane comprises a layer comprising a hydrophobic layer comprising microporous polyurethane having 4-way stretch.

9. The wearable article of claim 6, wherein the receptacle layer is configured for absorbing a hydrophilic treatment agent based on the receptable layer comprising a hydrophilic sub-layer coupled to a hydrophobic sub-layer.

10. The wearable article of claim 6, wherein the backing layer comprises super fine fibers of polyurethane formed into a 4-way stretch fabric.

11. The wearable article of claim 6, wherein the receptacle layer is configured for absorbing a hydrophilic treatment agent based on the receptacle layer comprising a mix of hydrophobic and hydrophilic components comprising different yarn types, at least one type comprising a synthetic yarn and another comprising a natural yarn.

12. The wearable article of 6, wherein the article comprises a garment.

13. The wearable article of claim 6, wherein the article comprises a sleeve or wrap for covering a selected area of the anatomy or physiology of the wearer.

14. The wearable article of claim 6, wherein the treatment delivery system corresponds to and mimics a nervous system pathway for a spine, neck, and/or back region of the wearer.

15. The wearable article of claim 6, wherein the treatment delivery system corresponds to and mimics a nervous system pathway for a finger, hand and/or arm region of the wearer.

16. The wearable article of claim 6, wherein the treatment delivery system corresponds to and mimics a nervous system pathway for a hips, abdomen and/or pelvic region of the wearer.

17. The wearable article of claim 6, wherein the treatment delivery system corresponds to and mimics a nervous system pathway for a shoulder, brachial plexus, collarbone and/or shoulder blade region of the wearer.

18. The wearable article of claim 6, wherein the treatment delivery system corresponds to and mimics a nervous system pathway for a toes, foot, and/or leg region of the wearer.

19. The treatment wearable article of claim 6, wherein the treatment delivery system corresponds to and mimics a nervous system pathway for a skull and/or jaw region of the wearer.

20. The wearable article of claim 6, wherein the treatment delivery system further comprises a treatment agent applied to the receptacle layer.

21. The wearable article of claim 6, wherein the wearable article includes a plurality of separated treatment delivery systems integrated in a plurality of different selected portions of the wearable article.

22. The wearable article of claim 6, wherein the receptacle layer is configured for absorbing oleophilic treatment agents based on the receptacle layer comprising an oleophilic sub-layer coupled to an oleophobic sub-layer.

23. The treatment wearable article of claim 6, wherein the receptacle layer is configured for absorbing hydrophilic and oleophilic treatment agents based on the receptacle layer comprising a hydrophilic and oleophilic layer coupled to the hydrophobic and oleophobic layer.

24. The wearable article of claim 6, wherein the nervous system pathway corresponds to a pathway in a hand area; wrist to collarbone area, a shoulder, brachial plexus, collar bone, and/or shoulder blade area; a hips, abdomen or pelvic area; a foot to thigh area; or a spine, neck, back, skull or jaw area of the wearer.

25. The wearable article of claim 6, wherein the backing layer extends past the edges of the receptacle layer.

* * * * *